United States Patent
Gross et al.

(10) Patent No.: US 6,241,713 B1
(45) Date of Patent: Jun. 5, 2001

(54) ABSORBENT STRUCTURES COATED WITH FOAMED SUPERABSORBENT POLYMER

(75) Inventors: James R. Gross, Cordova; Samuel C. Baer, Germantown, both of TN (US); Steve Leptick, Delta (CA); John P. Erspamer, Bartlett, TN (US)

(73) Assignee: Buckeye Technologies Inc., Memphis, TN (US)

( * ) Notice: Subject to any disclaimer, the term of this patent is extended or adjusted under 35 U.S.C. 154(b) by 0 days.

(21) Appl. No.: 09/211,934

(22) Filed: Dec. 15, 1998

Related U.S. Application Data

(60) Provisional application No. 60/088,453, filed on Jun. 8, 1998.

(51) Int. Cl.$^7$ ............................................. A61F 13/15
(52) U.S. Cl. ............................................. 604/368; 604/367
(58) Field of Search .................................. 604/368, 367

(56) References Cited

U.S. PATENT DOCUMENTS

| | | | |
|---|---|---|---|
| Re. 31,822 | * 2/1985 | Erickson et al. | 128/156 |
| 2,929,154 | 3/1960 | Finnegan . | |
| 3,224,986 | 12/1965 | Butler et al. | 260/9 |
| 3,332,909 | 7/1967 | Farnham et al. | 260/47 |
| 3,660,431 | 5/1972 | Hatch et al. | 260/332.3 |
| 3,669,103 | 6/1972 | Harper et al. | 128/156 |
| 3,749,738 | 7/1973 | Hatch et al. | 260/332.3 |
| 3,980,663 | * 9/1976 | Gross | 260/29.6 |
| 3,993,616 | * 11/1976 | Gross | 260/29.4 |
| 4,056,103 | 11/1977 | Kaczmarzyk | 128/285 |
| 4,076,673 | * 2/1978 | Burkholder, Jr. | 260/29.2 |
| 4,084,033 | 4/1978 | Drelich | 428/198 |
| 4,117,184 | * 9/1978 | Erickson et al. | 428/224 |
| 4,410,571 | * 10/1983 | Korpman | 427/385.5 |
| 4,424,247 | * 1/1984 | Erickson | 428/138 |
| 4,444,830 | * 4/1984 | Erickson | 428/246 |
| 4,529,739 | * 7/1985 | Scott et al. | 521/72 |
| 4,596,567 | 6/1986 | Iskra | 604/368 |
| 4,645,789 | 2/1987 | Dabi | 524/379 |
| 4,649,164 | * 3/1987 | Scott et al. | 521/149 |
| 4,721,647 | 1/1988 | Nakanishi | 428/283 |
| 4,813,945 | * 3/1989 | Le-Khac | 604/367 |
| 4,892,533 | * 1/1990 | Le-Khac | 604/368 |
| 4,914,170 | 4/1990 | Chang | 526/240 |
| 5,009,650 | 4/1991 | Bernardin | 604/378 |
| 5,041,104 | 8/1991 | Seal | 604/367 |
| 5,061,235 | * 10/1991 | Hogan | 600/21 |
| 5,100,397 | 3/1992 | Poccia | 604/365 |
| 5,128,082 | 7/1992 | Makoui | 264/112 |
| 5,135,792 | * 8/1992 | Hogan | 428/74 |
| 5,147,343 | 9/1992 | Kellenberger | 604/368 |
| 5,176,668 | 1/1993 | Bernardin | 604/368 |
| 5,188,624 | * 2/1993 | Young, Sr. et al. | 604/378 |
| 5,268,419 | 12/1993 | Stack | 524/831 |
| 5,336,554 | 8/1994 | Knight | 428/230 |
| 5,338,766 | * 8/1994 | Phan et al. | 521/63 |
| 5,378,528 | 1/1995 | Makoui | 428/219 |
| 5,389,181 | 2/1995 | Vukos et al. | 156/264 |
| 5,522,810 | 6/1996 | Allen et al. | 604/366 |
| 5,591,149 | * 1/1997 | Cree et al. | 604/378 |
| 5,607,414 | 3/1997 | Richards et al. | 604/378 |
| 5,645,542 | 7/1997 | Anjur | 604/368 |
| 5,763,067 | * 6/1998 | Bruggemann et al. | 428/317.9 |
| 5,800,419 | * 9/1998 | Soga et al. | 604/368 |
| 5,807,364 | 9/1998 | Hansen | 604/367 |
| 5,844,039 | 12/1998 | Scranton | 524/530 |
| 5,856,410 | * 1/1999 | Carrico et al. | 525/362 |
| 5,859,074 | * 1/1999 | Rezai et al. | 521/54 |
| 5,938,650 | * 8/1999 | Baer et al. | 604/368 |
| 5,944,706 | * 8/1999 | Palumbo et al. | 604/368 |
| 5,977,014 | * 11/1999 | Plischke et al. | 502/401 |
| 5,998,312 | 12/1999 | Kroesbergen . | |

FOREIGN PATENT DOCUMENTS

| | | |
|---|---|---|
| 0 689 817 A2 | 1/1996 | (EP) . |
| 0 690 077 A1 | 1/1996 | (EP) . |
| WO 94/22940A | 10/1994 | (WO) . |

OTHER PUBLICATIONS

Carr et al., *Interpolymer from Starch Xanthate and Polyamine–Epichlorohydrin Resin; Structure and Papermaking Application*, Journal of Applied Polymer Science, 17:721–735 (1973).

* cited by examiner

*Primary Examiner*—John G. Weiss
*Assistant Examiner*—Paul A Shanoski
(74) *Attorney, Agent, or Firm*—Darby & Darby

(57) ABSTRACT

An absorbent sheeted material containing a layer of a foamed hydrogel-forming polymer having superabsorbent properties coated on the surface of a sheeted fibrous absorbent material suitable for use in disposable absorbent products and methods of making thereof are disclosed.

13 Claims, No Drawings

ABSORBENT STRUCTURES COATED WITH FOAMED SUPERABSORBENT POLYMER

This patent application claims priority under 35 U.S.C. §119 from the provisional application Ser. No. 60/088,453 filed Jun. 8, 1998, incorporated herein by reference in its entirety.

FIELD OF THE INVENTION

This invention relates to a process of making a superabsorbent roll good suitable for fabrication into thin disposable absorbent hygiene articles such as for example pantyliners and sanitary napkins and to the products prepared according to the process of the invention. According to the invention, an aqueous solution of a hydrogel-forming polymer having superabsorbent properties upon drying and curing is foamed to several times its original volume and applied to a sheeted fibrous absorbent material to form a distinct, porous layer of a superabsorbent material on the surface of the sheeted fibrous absorbent material.

BACKGROUND OF THE INVENTION

Conventional absorbent articles such as baby diapers, adult incontinence devices, and feminine napkins are typically made with a cellulose fiber fluff-based absorbent core sandwiched between a liquid pervious top sheet, which allows the unobstructed passage of fluid to the absorbent core, and a liquid impervious backing sheet usually of plastic material, which contains the absorbed fluid and prevents it from passing through the absorbent core and soiling the undergarments of the wearer of the absorbent article.

The absorbent core of these absorbent articles is typically constructed of defiberized wood pulp with or without superabsorbent polymer granules. The absorbent core is typically formed on a pad-forming unit of a converting machine on a carrier tissue to facilitate processing. Some absorbent core forming units are equipped with layering capability in which a second discrete fluff layer may be laid over a primary fluff-based absorbent layer to form a multi-layer absorbent structure. In these absorbent structures, the primary layer may include superabsorbent polymer granules. With regard to conventionally produced absorbent structures, reference is made to U.S. Pat. Nos. 5,009,650, 5,378,528, 5,128,082, 5,607,414, 5,147,343, 5,149,335, 5,522,810, 5,041,104, 5,176,668, 5,389,181, and 4,596,567, the disclosures of which are hereby incorporated herein by reference.

In recent years, market demand for thinner and more comfortable absorbent articles has increased. Ultra-thin feminine napkins are no longer constructed from loose wood pulp, which tends to give a bulky product, but with roll good-based air-laid absorbent cores in which a roll of preformed absorbent core material is unwound directly onto the absorbent pad-making machine without the defiberization step required for fluff-based products. The roll good-based approach results in a product thinness, which can not be achieved by loose fluff-based technology.

It is known in the art, as described in U.S. Pat. Nos. 3,669,103 and 3,670,731 for example, that carboxylic polyelectrolytes may be cross-linked to create hydrogel-forming materials, now commonly referred to as superabsorbents. These materials are used to enhance the absorbency of disposable absorbent articles. The use of continuous and discontinuous coatings of superabsorbent polymers on various materials is described, for example, in U.S. Pat. Nos. 4,076,673, and 5,071,681 discloses preparation of an air-laid fibrous web and application of a water-insoluble binder to one surface of the web and a water-soluble polymer capable of forming a superabsorbent to the other surface of the web. U.S. Pat. No. 4,444,830 discloses a liquid superabsorbent precursor solution, which is chemically foamed and applied to a base fluffing material, which coated fluffing material is then dried, disintegrated and mechanically worked into a fibrous fluff matrix containing absorbent polymer platelets distributed throughout the matrix.

The above-mentioned approaches for coating fibrous and non-woven materials with superabsorbent-forming compositions cause stiffness of the coated materials due to the inherent brittleness of polyelectrolytes. Humectants such as glycerol may be used to overcome this problem, however, humectants can only plasticize polyelectrolytes in the presence of a substantial amount of water. Maintaining the necessary moisture content is difficult in dry climates. Furthermore, spraying a dilute liquid superabsorbent precursor solution onto an air-laid web may cause deep polymer penetration into the web so that the superabsorbent polymer is not a discrete layer on the surface of the web but a diffuse coating on the fibers of the web.

It has now been surprisingly discovered that it is not necessary nor even desirable to have the superabsorbent polymer material dispersed throughout the absorbent composite for the superabsorbent to work in its intended fashion. Indeed, having the superabsorbent concentrated in a distinct layer, which may be placed (in a disposable absorbent product) away from the source of the liquid insult, provides more efficient utilization of the fibrous material in the absorbent product for initially imbibing and then transporting the fluid. This result is accomplished by foaming a composition containing a water soluble polymer capable of forming a superabsorbent polymer upon drying and curing and applying the foam onto the absorbent web.

SUMMARY OF THE INVENTION

The present invention relates to an absorbent sheeted material containing a layer of a foamed hydrogel-forming polymer having superabsorbent properties coated on the surface of a sheeted fibrous absorbent material suitable for use in disposable absorbent products and to methods of making thereof.

Accordingly, in one aspect of the invention, an absorbent sheeted material containing a layer of a foamed hydrogel-forming polymer coated on the surface of a sheeted fibrous absorbent material is provided.

In another aspect of the invention, a disposable absorbent product prepared by using the absorbent sheeted material of the invention is provided.

In yet another aspect of the invention, a method for making the absorbent sheeted product of the invention is provided.

DETAILED DESCRIPTION OF THE INVENTION

All patents, patent applications and references cited herein are incorporated hereby by reference. In case of inconsistencies, the present disclosure governs.

The present invention relates to an absorbent sheeted material, and a method of preparing the absorbent sheeted material, suitable for fabrication into thin disposable absorbent hygiene articles such as, for example, pantyliners and sanitary napkins.

The absorbent sheeted material of the invention comprises (i) a sheeted fibrous absorbent material and (ii) a foamed hydrogel-forming polymeric material coated on the surface of the sheeted fibrous absorbent material.

The "sheeted fibrous absorbent material" is any absorbent fibrous matrix in the form of a sheet and is referred to hereinafter as "fibrous structure." Such fibrous structures may be prepared by methods well known in the art such as for example by using air-laying or wet laying processes. Representative examples of such fibrous structures are: air-laid non-wovens prepared from individualized wood fibers alone or in admixture with synthetic fibers and bonded using adhesives or thermal bonding fibers or powders. The fibrous structure could also be a composite of several layers of fibers. The fibrous structure may contain any natural fiber, including wood fibers such as for example, air laid-fluff cellulose, chemically modified cellulose fibers, cross-linked cellulose fibers, or cotton linter fibers. Synthetic fibers, such as polyester fibers, such as polyethyleneterephthalate ("PET"), polypropylene, nylon and acrylic, may also be used.

The fibers in the fibrous structure may be latex-bonded and/or thermally-bonded. Other methods known in the art for creating physical entanglements, such as needle punching and hydroentangling, may also be used.

A latex-bonded fibrous structure contains latex, such as for example polymers and copolymers of alkylacrylate, vinyl acetate and styrene-butadiene. A thermally-bonded fibrous structure may contain thermoplastic fibers or powder, which are well known in the art, and which are known to provide bonding upon heating to the melting point of the thermoplastic fiber or powder. In one embodiment of the invention, the fibrous structure of the invention is an air-laid non-woven either latex-bonded or thermally bonded.

The "foamed hydrogel-forming polymeric material" refers to a highly absorbent material having a property of forming a gel upon liquid absorption. It contains a foamed water soluble polymer reacted with at least one cross-linking agent.

The water-soluble polymer for use in the present invention is capable of forming a superabsorbent upon cross-linking, such as for example upon drying and curing in an oven. A "superabsorbent" is a water soluble polymer which has been cross-linked to render it water insoluble but still swellable. The cross-linked polymer may swell to about 15 times or more its own weight in physiological saline solution.

The polymer useful in the practice of the invention generally may be any physiologically compatible, hydrophilic polymer. According to one embodiment of the present invention, an aqueous solution of a carboxylic polyelectrolyte may be used in the preparation of the foamed hydrogel-forming polymeric material.

In one preferred embodiment, polyelectrolytes useful in the invention are ammonium or alkali metal salts of homopolymers of acrylic or methacrylic acid and copolymers with one or more ethylenically unsaturated comonomers.

In one embodiment, the polyelectrolyte is a partially saponified polyacrylate polymer. Before the saponification, the polymer may be prepared by reacting a mixture of monomers which may comprise (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid; and (3) 0 to 15 percent by weight of an omega hydroxyalkyl acrylate wherein the hydroxyalkyl group has from 1 to 4 carbons.

Examples of useful alkyl acrylates include methyl acrylate, ethyl acrylate, propyl acrylate, butyl acrylate, and hexyl acrylate. Examples of useful alkyl methacrylates include methyl methacrylate, ethyl methacrylate, hexyl methacrylate, octyl methacrylate and decyl methacrylate. Examples of useful omega hydroxyalkyl acrylates include 2-hydroxyethyl acrylate, hydroxymethyl acrylate, and 4-hydroxy butyl acrylate.

The olefinically unsaturated carboxylic acids useful in this invention are mono- or polycarboxylic acids. Examples of monocarboxylic acids include acrylic acid, methacrylic acid, crotonic acid, and isocrotonic acid. Examples of polycarboxylic acids include maleic acid, fumaric acid, and itaconic acid.

A list of applicable polymers which could be prepared from readily available monomers and converted into their salt form is as follows: acrylic acid—acrylate copolymers; acrylic acid—acrylamide copolymers; acrylic acid—olefinic copolymers; polyacrylic acid; acrylic acid—vinyl aromatic copolymers; acrylic acid vinyl ether copolymers; acrylic acid—vinyl acetate copolymers; acrylic acid—vinyl alcohol copolymers and copolymers of methacrylic acid with all the above comonomers.

In one preferred embodiment of the invention, the carboxylic polyelectrolyte is the half sodium salt of the alternating copolymer of an alpha-olefin and maleic anhydride, where the alpha olefin is ethylene, propylene, 1-butene, isobutylene, styrene, or mixtures of two or more thereof. In another preferred embodiment, the carboxylic polyelectrolyte is poly(acrylic acid) or a copolymer of acrylic acid with an ethylenically unsaturated monomer, in which the acid moieties are 40–90 percent neutralized with sodium hydroxide.

Other hydrophilic polymers may also be employed, such as acrylic copolymer and starch/graft copolymers. Also useful are water-insoluble alkali salts of saponified, gelatinized starch/polyacylonitrile graft polymers taught in U.S. Pat. Nos. 3,997,484 and 4,405,387.

Cross-linking agents that may be used for preparing the hydrogel-forming polymeric material of the invention are well known in the art.

Illustrative examples of the polyfunctional cross-linking agents useful in this invention to convert the above polyelectrolytes into water-swellable polymers are set forth in U.S. Pat. Nos. 2,929,154; 3,224,986; 3,332,909; and 4,076,673 incorporated herein by reference. These polyfunctional cross-linking agents are generally known as polyamide-polyamine epichlorohydrin adducts. Similar cross-linking agents are commercially available Kymene 557 and Polycup 172 (obtained from Hercules Incorporated, Wilmington, Del.). The structure of these adducts is well known and is described in M. E. Coor et al., *Journal of Applied Polymer Science*, Vol. 17, pages 721–735 (1973).

Illustrative examples of the difunctional agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as cross-linking agents are monomeric amine-epihalohydrin adducts. Sulfonium zwitterions described in U.S. Pat. Nos. 3,660,431; 3,749,737; and 3,749,738, incorporated herein by reference, may also be used.

The cross-linking agents may be used in an amount from about 0.05 to about 5.0 percent based on the weight of the polyelectrolyte used. This is generally sufficient to cause the polyelectrolyte to become lightly cross-linked. However, this range may vary for each polyelectrolyte in order to adjust the absorbency of the final cross-linked material and can be determined using routine experimentation.

A hydrogel-forming polymeric material suitable for use in the invention may absorb greater than about 15 times its weight of synthetic or natural urine. Preferably, the absorbency should be in the range from about 30–60 grams of urine per gram of polyelectrolyte or in the range of 90–250 grams of deionized water per gram of polyelectrolyte.

The hydrogel-forming polymeric material of the invention is in the form of a foam. The foam for use in the absorbent sheeted structures of the invention is prepared from a polymer solution by stirring the solution rapidly until the foam reaches a desirable volume. Any other foam generating equipment may be used.

The polymer solution may be prepared by dissolving a polymer in water. In one embodiment, the polymer solution contains a cross-linking agent, which may be added before or after foaming provided that the cross-linking agent is evenly distributed.

To facilitate foaming, a perforated paddle with a subsurface stream of nitrogen may be used for stirring. The foaming is continued until the foam volume is from about 1.5 to about 10 times the original liquid volume, and preferably about three to four times the original volume.

After the desired volume is achieved, the foam is ready to use or it may be first blended with a latex to flexibilize the dried and cured polymer. The latex may also be added prior to foaming.

The foamed hydrogel-forming polymeric coating of the invention may contain a rubbery aqueous dispersion in the amount effective to flexibilize the resulting polymer coating. The rubbery aqueous dispersion may be a natural or synthetic polymer latex. Examples of the synthetic polymer are polymers and copolymers of alkylacrylates, vinyl acetate, and styrene-butadiene. The latex is generally used at from about 5 to about 50 percent by weight of the coating to significantly improve the flexibility of the coating, preferably from about 15 to about 20 percent by weight.

In one embodiment of the invention, the superabsorbent roll good of the invention contains a distribution layer. The distribution layer may be as generally known in the art. For example, the matrix fibers of the distribution layer may be (i) fluff cellulose fibers (e.g. Buckeye Foley fluff available from Buckeye Technologies, Inc., Memphis, Tenn.), (ii) chemically modified fluff cellulose (e.g. cross-linked cellulose) or highly purified cellulose (e.g. Buckeye HPF), or (iii) blends thereof. The fibers may be latex-bonded fibers, thermally-bonded fibers or a combination thereof.

The present invention also relates to a process for preparing the absorbent sheeted material of the invention. In one embodiment of the invention, a polymeric material suitable for use in the invention is first dissolved in water. The polymer may be dissolved at a concentration of about 5% to about 20% by weight. Then, an effective amount of a cross-linking agent capable of reacting with carboxyl or carboxylate groups of the polymer upon drying is added into the polymer solution. The resulting solution is then foamed in a foam generator to a desired foam volume, for example from 1.5 to 10 times the volume of the original solution. The foam is then applied to a sheeted fibrous absorbent material by spraying, using a doctor blade or any other suitable method. The weight of the foam needed to yield a desired level of polymer loading can be calculated for example based on the amount of the dried (non-foamed) polymer generally used in the art. For example, the foam volume may be calculated to achieve about 30–40 gsm of polymer. In order to have 40 gsm superabsorbent on a 14×14 inch pad, the total solids needed is about 5.06 grams (50.6 grams of 10% solids foam). The foam-coated material is then dried to remove the solvent and to cause the cross-linking of the polyelectrolyte. During the drying step, the cross-linker is activated and the polymer becomes superabsorbent. Any suitable method of drying can be used. For example, the coated material may be dried in an oven at about 60 to about 160° C., preferably about 125° C.

The hydrogel-forming polymeric materials according to the present invention are suited to absorb many liquids, such as water, saline, synthetic urine, and body liquids, such as urine, menses, and blood, and are suited for use in disposable absorbent products, such as diapers, adult incontinent products, and bed pads; in catamenial devices such as sanitary napkins, and tampons; and in other absorbent products such as wipes, bibs, wound dressings, and surgical capes or drapes. Accordingly, disposable absorbent products containing a foamed hydrogel-forming polymeric material of the invention are also within the scope of the present invention. These disposable absorbent products may be prepared according to the methods well known in the art using roll goods containing the foamed hydrogel-forming polymeric material of the invention coated on a sheeted fibrous absorbent material. In one preferred embodiment, the foamed hydrogel-forming material of the invention is positioned further away from the body of the wearer relative to the sheeted fibrous absorbent material.

The advantage of using a foamed hydrogel-forming polymeric material (rather than a diluted polymer solution) for coating the fibrous structure is in that a significant foam volume needed to completely coat the fibrous structure can be produced without using an excessive volume of water, which needs to be removed. Furthermore, polymer penetration into the fibrous structure is limited by foam viscosity. In contrast, spraying a dilute polymer solution onto the fibrous structure causes penetration of the polymer and formation of a less discrete layer. Finally, the polymer can be handled in a concentrated form since the bulk of the foam volume is air, not water.

Another advantage of the present invention is in the use of a rubbery polymer to flexibilize the dried hydrogel-forming polymer. The dispersed rubbery phase facilitates bending and flexing of the polymer coating without shattering. The flexible polymer coating can function as the only superabsorbent polymer in those products that are intended for applications in which the volume of fluid to be absorbed is not large.

Yet another advantage of the present invention is that the superabsorbent material forms a discrete layer in which the influx of fluid and the swelling of the superabsorbent is not obstructed by the presence of the fibers. Since the superabsorbent is a substantially continuous, although somewhat porous, layer and not discrete individual particles, the dry containment of the superabsorbent during and after the preparation of the final product is improved. Accordingly, since dusty, abrasive superabsorbent powders are not used around the machinery, costly shutdowns for periodic cleaning are minimized.

The present invention is further described in the following non-limiting examples.

EXAMPLE

Preparation of the Superabsorbent Polymer Precursor Solution

The sodium half salt of poly(isobutylene-co-maleic anhydride) from Kuraray International (ISOBAM-10 lot no. 825271) is prepared in a 1000 ml resin flask equipped with paddle stirrer, reflux condenser, temperature controller, and heating mantle at 25% solids by suspending 154 g (1.0 mol) of copolymer in 582 grams of distilled water containing 0.3 grams of Neodol 25-9 (non-ionic surfactant) by Shell Chemical Company. Sodium hydroxide in the prill or bead form (40.0 grams, 1.0 mol, from Aldrich Chemical lot no. 02420HQ) is added to the slurry and the temperature is raised to 85° C. Heating and stirring is continued until the polymer dissolves, about 4 hours.

Preparation of Superabsorbent Precursor Foam

The 25% solution of half-neutralized ISOBAM-10 (50.0 grams) is diluted to 10% solids with 125 grams distilled water. 0.13 grams of sodium lauryl sulfate (anionic surfactant) is added to stabilize the foam. The cross-linker (KYMENE 557 by Hercules) 1.0% by weight polymer (1.25 grams of 10% solution) is added and the combination is stirred rapidly with a perforated paddle with a sub-surface stream of nitrogen to facilitate foaming. The stirring is continued until the foam volume is about three times the original liquid volume. The foam is ready to use or may be blended with a latex to flexibilize the dried and cured polymer. If a latex is added, the water in the latex may be subtracted from the distilled water in the recipe.

Coating of Nonwovens

The weight of foam calculated to yield the desired polymer loading is spread evenly on the non-woven and dried at 125° C. in a laboratory convection oven. For example, in order to have 40 gsm superabsorbent on a 14—14 inch pad, the total solids needed is 5.06 grams (50.6 grams of 10% solids foam). During the drying step, the cross-linker is activated and the polymer becomes superabsorbent.

Saturated Capacity

Samples are cut into 2.25-inch squares, weighed and immersed in saline (0.9% NaCl) for 20 minutes. The pad is allowed to drain for five minutes before reweighing. The absorbency of the pad (grams saline absorbed per gram of pad) is the total weight of the wet pad minus the weight of dry pad divided by the weight of the dry pad.

Retention

The pads from the absorbency test are placed under a load of 0.9 psi for five minutes. The pressed pads are weighed and the retention is calculated the same way as absorbency.

Experimental Results

A substrate 80 gsm air-laid non-woven was prepared on a pilot line from cellulose fluff bonded with a styrene-butadiene latex. The smooth (wire) side of the non-woven was treated with superabsorbent liquid precursor, foam, and foam/latex. The particular latex used in these examples was RHOPLEX® HA-8 from Rohm and Haas.

As shown in Table 1, the control pad retains less fluid under pressure than the foam-coated air-laid pads. In other words, the foam coating occupies void volume which would ordinarily be filled with fluid under no-load conditions so that the advantage of foaming is only apparent under high load which expresses ungelled fluid from the pad. Since the coated pads weigh more than the control, the absolute absorbency is even greater than indicated by the gram per gram capacity. One gram of control pad retains 1.7 grams of saline under pressure. If coated with 30 gsm of foamed superabsorbent, the pad increases in weight to 1.375 grams and now retains 4.0 grams of saline (2.9 g/g), an actual increase in absorbency of 135% over the same pad without the coating. Similarly, for Example 2, an actual absorbency of 3.1 grams of saline for one gram of control pad which is subsequently treated (an increase of 82%). Comparative Example 1 shows that coating the control pad with unfoamed liquid superabsorbent formulation is not as effective in producing high retention under pressure. While one gram of pad increases to 1.375 grams as before, since the g/g capacity is only 1.8, the actual absorbency increases to 2.5 grams of saline, which is an increase of 45.5%.

TABLE 1

| sample | gsm fiber | gsm Sap foam solids | gsm latex solids | gsm SAP liquid solids | Sat. Cap g/g | 0.9 psi Retention g/g |
|---|---|---|---|---|---|---|
| Control 1 | 80 | | | | 15.7 | 1.7 |
| Example 1 | 80 | 30 | | | 15.8 | 2.9 |
| Example 2 | 80 | 30 | 15 | | 13.2 | 2.0 |
| Comparative Example 1 | 80 | | | 30 | 15.6 | 1.8 |

What is claimed is:

1. An absorbent sheeted material comprising:
   a. a sheeted fibrous absorbent material and
   b. a foamed hydrogel-forming polymeric material coated on the surface of the sheeted fibrous absorbent material, to form a continuous layer, wherein the sheeted fibrous absorbent material is an air-laid non-woven which is both latex-bonded and thermally bonded.

2. The absorbent sheeted material of claim 1 wherein the foamed hydrogel-forming polymeric material comprises a carboxylic polyelectrolyte.

3. The absorbent sheeted material of claim 2 wherein said carboxylic polyelectrolyte is the half ammonium or alkali metal salt of the alternating copolymer of an alpha-olefin and maleic anhydride, and wherein the alpha olefin is selected from a group comprising ethylene, propylene, 1-butene, isobutylene, and styrene, and mixtures of two or more alpha-olefins.

4. The absorbent sheeted material of claim 2 wherein said carboxylic polyelectrolyte is poly(acrylic acid) or a copolymer of acrylic acid with an ethylenically unsaturated monomer and wherein the acid moieties are 40–90 percent neutralized with ammonia or an alkali metal hydroxide or carbonate.

5. A process for preparing an absorbent sheeted material comprising the steps of:
   a. preparing a solution of a carboxylic polyelectrolyte;
   b. adding an effective amount of a cross-linking agent to the solution;
   c. foaming the solution;
   d. applying the solution to a sheeted fibrous absorbent material; and
   e. drying the foam-coated material, wherein the solution includes a rubbery aqueous polymer latex dispersion in an amount effective to flexibilize the resulting polymer coating, wherein said dispersion is present in an amount of from about 5 to about 50 percent by weight of the foamed coating.

6. The process of claim 5, wherein said synthetic polymer latex is selected from the group consisting of polymers and copolymers of alkylacrylate, vinyl acetate, and styrene-butadiene.

7. A disposable absorbent product comprising an absorbent sheeted material of claim 1.

8. A disposable absorbent product comprising an absorbent sheeted material of claim 2.

9. A disposable absorbent product comprising an absorbent sheeted material of claim 3.

10. A disposable absorbent product comprising an absorbent sheeted material of claim 4.

11. The disposable absorbent product of claim 7 wherein said product is a diaper.

12. The disposable absorbent product of claim 7, wherein said product is a sanitary napkin.

13. The disposable absorbent product of claim 7, wherein said product is an adult incontinent product.

* * * * *